United States Patent [19]

Jessel, Jr. et al.

[11] Plant 4,554

[45] Jun. 24, 1980

[54] CHRYSANTHEMUM PLANT CULTIVAR NAME: RADIANT

[75] Inventors: Walter H. Jessel, Jr., Grantsville, W. Va.; William E. Duffett, Salinas, Calif.

[73] Assignee: Yoder Brothers, Inc., Barberton, Ohio

[21] Appl. No.: 10,855

[22] Filed: Feb. 9, 1979

[51] Int. Cl.[2] ..... A01H 5/00

[52] U.S. Cl. ..... Plt./74

[58] Field of Search ..... Plt./74

*Primary Examiner*—Robert E. Bagwill

*Attorney, Agent, or Firm*—Donald D. Jeffery

[57] ABSTRACT

A chrysanthemum plant known by the cultivar name Radiant and particularly characterized as to uniqueness by the combined characteristics of flat capitulum form; spooned daisy capitulum type; dark red bronze abaxial ray floret color; golden bronze adaxial ray floret color; diameter across face of capitulum ranging from 75 to 100 mm. at maturity; uniform nine week photoperiodic flowering response to short days; tall plant height when grown as a pinched spray pot; and semi-upright branching pattern.

7 Drawing Figures

The present invention comprises a new and distinct cultivar of *Chrysanthemum morifolium,* Ramat., hereinafter referred to by the cultivar name Radiant.

Radiant is a product of a planned breeding program which had the objective of creating new chrysanthemum cultivars with spoon daisy capitulum type, with bronze ray floret color, with eight or nine week flowering response, and with the ability to produce commercially acceptable quality in year round pot mum programs. Such traits in combination were not present in previously available commercial cultivars.

Radiant was originated from a cross made in a controlled breeding program in Barberton, Ohio in 1975. The female parent was #74077002 (unnamed seedling), a lavender single originated by the present inventors from a cross between #67586001 (unnamed seedling) and #71078021 (unnamed seedling). The male parent of Radiant was #72220003 (unnamed seedling), a lavender decorative originated by the present inventors from a cross between #70042004 (unnamed seedling) and #71071009 (unnamed seedling). #67586001, #71078021, #70042004 and #71071009 are products of the breeding program of the present inventors.

Radiant was discovered and selected as one flowering plant within the progeny of the stated cross by Walter H. Jessel, Jr. and William E. Duffett on Nov. 12, 1976 in a controlled environment in Barberton, Ohio.

The first act of asexual reproduction of Radiant was accomplished when vegetative cuttings were taken from the initial selection in February, 1977 in a controlled environment in Barberton, Ohio, by a technician working under formulations established and supervised by William E. Duffett. Continued asexual reproduction by vegetative cuttings for evaluative tests in flowering and stock programs in conjunction with horticultural examination of selected units initiated November, 1977 has demonstrated that the combination of characteristics as herein disclosed for Radiant are firmly fixed and are retained through successive generations of asexual reproduction.

Radiant has not been observed under all possible environmental conditions. The phenotype may vary significantly with variations in environment such as temperature, light intensity, and daylength. The following observations, measurements, and comparisons describe plants grown in Salinas, Calif. under greenhouse conditions which approximate those generally used in commercial practice.

The following traits have been repeatedly observed and are determined to be basic characteristics of Radiant which in combination distinguish this chrysanthemum as a new and distinct cultivar:

(1) Flat capitulum form.

(2) Spooned daisy capitulum type.

(3) Red bronze abaxial ray floret color and golden bronze adaxial ray floret color.

(4) Diameter across face of capitulum ranging from 75 to 100 mm. at maturity.

(5) Uniform nine week photoperiodic flowering response to short days.

(6) Tall plant height (requiring 1–2 long day weeks prior to pinch and short days, and two applications 2500 ppm B-9 SP 14 to 21 days after the beginning of short days to attain a flowered plant height of 30 to 45 cm.).

(7) Semi-upright branching pattern.

The accompanying photographic drawings show typical inflorescence and foliage characteristics of Radiant, with colors being as nearly true as possible with illustrations of this type. Sheet 1 is a color photograph of the inflorescence of Radiant. Sheet 2 is a black and white photograph of three views of the capitulum of Radiant. Sheet 3 is a black and white photograph of the foliage of Radiant at three stages of growth.

Of the many cultivars known to the present inventors, the most similar in comparison to Radiant are Jamboree, disclosed in U.S. Plant Pat. No. 4,156, and Dramatic, disclosed in U.S. Plant Pat. No. 3,189. Reference is made to attached Chart A which compares certain characteristics of Radiant to those same characteristics of Jamboree and Dramatic. General comparisons are as follows:

(1) In comparison to Jamboree, Radiant has different ray floret color, smaller diameter across face of capitulum, and greater responsiveness to B-9 SP for height control. The capitulum form, capitulum type, branching pattern, plant height, and flowering response period of Radiant are similar to those same characteristics of Jamboree.

(2) In comparison to Dramatic, Radiant has different ray floret color, different capitulum type, and larger diameter across face of capitulum. The capitulum form, branching pattern, plant height, responsiveness to B-9 SP for height control, and flowering response period of Radiant are similar to those same characteristics of Dramatic.

In the following description, color references are made to A Limit Color Cascade, by the Munsell Company, 1972 edition. The color values were determined between 1:30 and 2:00 P.M. on Nov. 11, 1978 under 100 foot-candle light intensity at Salinas, Calif.

Botanical classification: *Chrysanthemum morifolium,* Ramat., cv Radiant.

INFLORESCENCE

A. Capitulum:
- *Form.*—Flat.
- *Type.*—Spooned daisy.
- *Diameter across face.*—75 to 100 mm.

B. Corolla of ray florets:
- *Color (general tonality).*—Light golden bronze (27-7 overlaid lightly with 28-11) with red bronze (36-14) spoon.
- *Color (abaxial).*—36-14 (inside spoon tip).
- *Color (adaxial).*—28-2 to 28-3 overlaid slightly with 36-14 (tube).
- *Persistence.*—Resists shatter.

C. Corolla of disc florets:
- *Color.*—20-10 (immature) to 26-4 (mature).

D. Reproductive organs:
- *Androecium.*—Present disc florets only; moderate pollen.
- *Gynoecium.*—Present both ray and disc florets.

PLANT

A. General appearance:
- *Branching pattern.*—Semi-upright.
- *Height.*—Tall.

B. Foliage:
- *Color (abaxial).*—Approximately 20-14.
- *Color (adaxial).*—Approximately 20-13 overlaid with white.

CHART A

COMPARISON OF RADIANT, JAMBOREE, AND DRAMATIC.

| CULTIVAR | RAY FLORET COLOR | CAPITULUM FORM & TYPE | BRANCHING PATTERN |
|---|---|---|---|
| Radiant | Red bronze flare and golden bronze tube | Flat spooned daisy | Semi-upright |
| Jamboree | Orange bronze flare and yellow bronze tube | Flat spooned daisy | Semi-upright |
| Dramatic | Golden bronze to yellow | Flat daisy | Semi-upright |

| CULTIVAR | DIAMETER ACROSS FACE OF CAPITULUM | PLANT HEIGHT | FLOWERING RESPONSE PERIOD |
|---|---|---|---|
| Radiant | 75 to 100 mm. | Tall, responsive to B9 SP | 9 week |
| Jamboree | 100 to 110 mm. | Tall, not responsive to B-9 SP | 9 week |
| Dramatic | 65 to 90 mm. | Tall, responsive to B-9 SP | 9 week |

COMPARISONS MADE OF PLANTS GROWN AS PINCHED SPRAY POTS IN SALINAS, CALIFORNIA.

We claim:

1. A new and distinct cultivar of *Chrysanthemum morifolium,* Ramat., plant as shown and described, known by the cultivar name Radiant and particularly characterized as to uniqueness by the combined characteristics of flat capitulum form; spooned daisy capitulum type; red bronze abaxial and golden bronze adaxial ray floret color; diameter across face of capitulum ranging from 75 to 100 mm. at the maturity; uniform nine week flowering response; tall plant height; and semi-upright branching pattern.

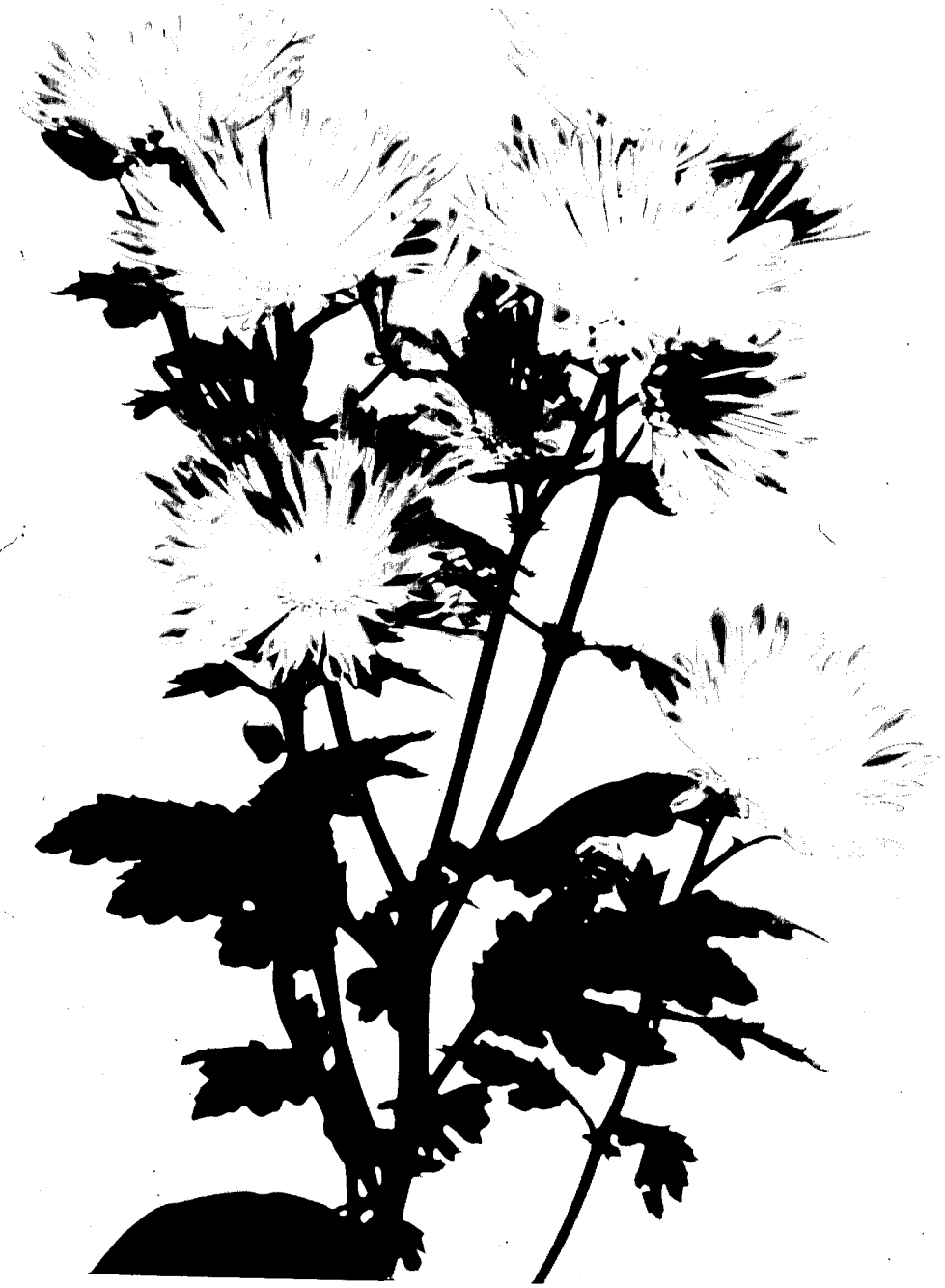

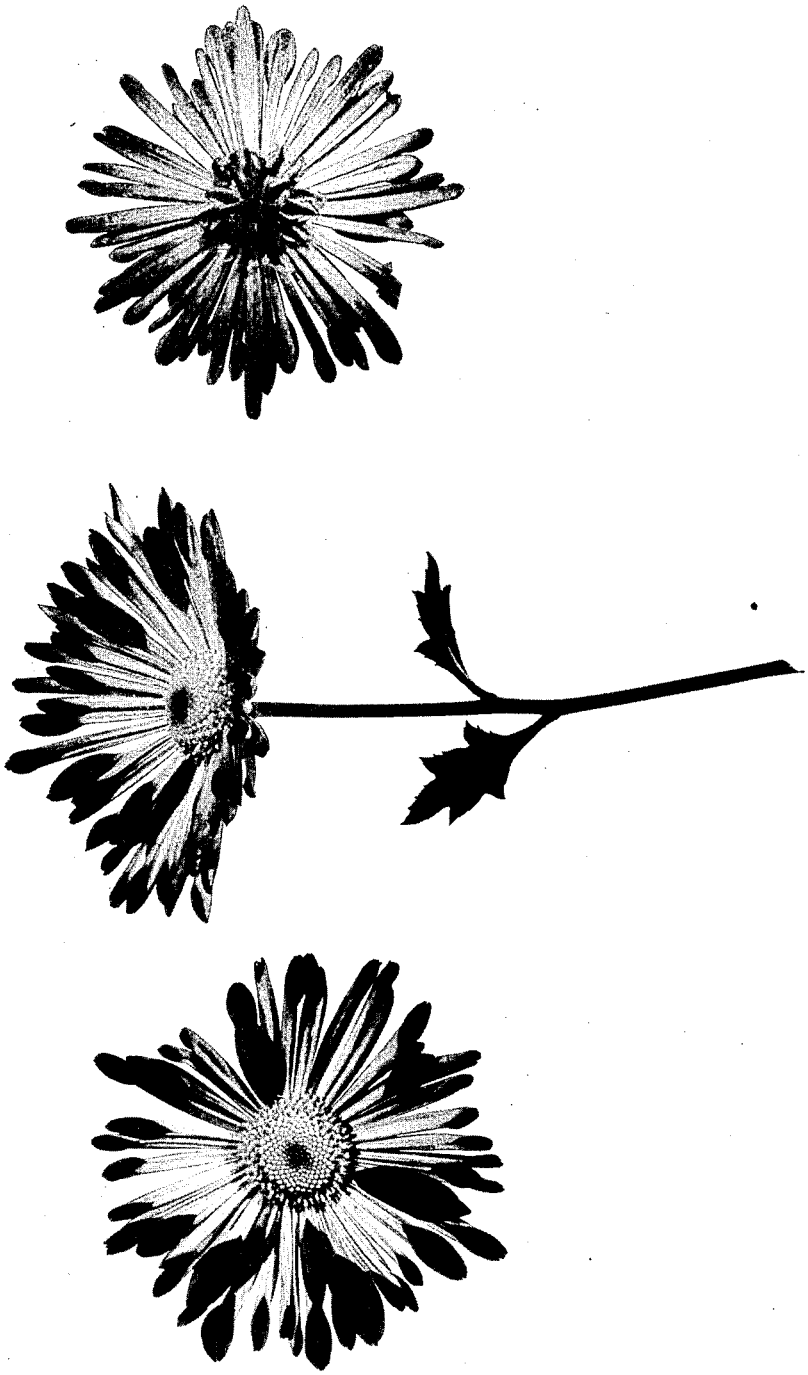

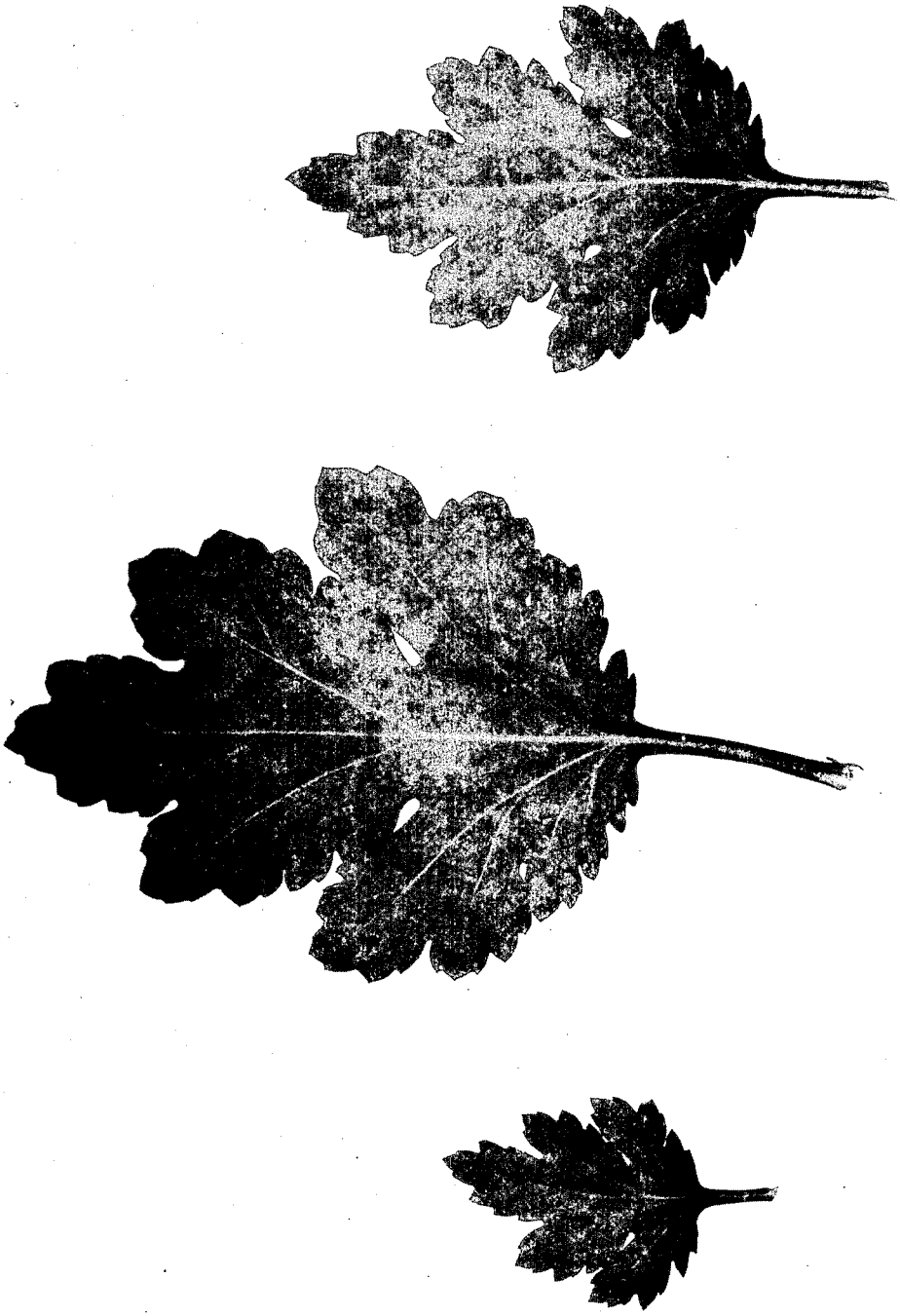

* * * * *